(12) United States Patent
Idman et al.

(10) Patent No.: US 6,394,095 B1
(45) Date of Patent: May 28, 2002

(54) SURGICAL DRAPE WITH A LIQUID BARRIER

(75) Inventors: Patrik Idman, Hallingsjo; Ove Berdal, Molnlycke, both of (SE)

(73) Assignee: Molnlycke Health Care AB, Gothenburg (SE)

( * ) Notice: Subject to any disclaimer, the term of this patent is extended or adjusted under 35 U.S.C. 154(b) by 0 days.

(21) Appl. No.: 09/720,875

(22) PCT Filed: Jun. 22, 1999

(86) PCT No.: PCT/SE99/01126

§ 371 (c)(1),
(2), (4) Date: Feb. 27, 2001

(87) PCT Pub. No.: WO00/00101

PCT Pub. Date: Jan. 6, 2000

(30) Foreign Application Priority Data

Jun. 30, 1998 (SE) ................................................. 9802343

(51) Int. Cl.[7] .............................................. A61B 19/00
(52) U.S. Cl. ....................................... 128/849; 128/853
(58) Field of Search ................................. 128/849–856

(56) References Cited

U.S. PATENT DOCUMENTS

| 3,538,912 | A | * | 11/1970 | Becker | 128/853 |
| 3,763,857 | A | * | 10/1973 | Schrading | 128/853 |
| 3,921,627 | A | * | 11/1975 | Wilson | 128/853 |
| 4,873,997 | A | * | 10/1989 | Marshall | 128/853 |
| 5,832,927 | A | * | 11/1998 | Wijesinghe | 128/853 |

FOREIGN PATENT DOCUMENTS

WO     WO 95/10242    *   4/1995

* cited by examiner

*Primary Examiner*—Michael A. Brown
(74) *Attorney, Agent, or Firm*—Young & Thompson

(57) ABSTRACT

The present invention relates to a surgical drape that includes a liquid-absorbent top sheet (1) and a liquid-impervious sheet (2) immediately beneath the top sheet. The liquid-impervious sheet faces towards a patient when the drape is in use. According to the invention, at least one string of hotmelt glue (5) is disposed on the surface of the drape, this hotmelt glue extending from the upper side of the top sheet, through said top sheet and bonds with the liquid-impervious sheet.

5 Claims, 1 Drawing Sheet

SURGICAL DRAPE WITH A LIQUID BARRIER

FIELD OF INVENTION

The present invention relates to a surgical drape that includes a liquid-absorbent top sheet and a liquid-impervious sheet placed immediately beneath the top sheet, said liquid-impervious sheet being turned to face towards a patient when the surgical drape is used.

BACKGROUND OF INVENTION

Applicant retails a surgical drape designated Klinidrape® which is comprised of a three-sheet laminate, i.e. a liquid-impervious nonwoven top sheet, a liquid-impervious intermediate sheet comprised of polyethylene, and a bottom absorbent sheet comprised of cellulose wadding. The top sheet is intended to absorb blood and other fluids discharged or flowing from the surgical area, in order to prevent contamination of theatre personnel and the operating theatre itself. The plastic film forms a barrier against the transportation of fluid-carried bacteria between the patient and the surgical area and the undersurface of the sheet of cellulose wadding is intended to enhance patient comfort, by absorbing perspiration and preventing direct contact of the patient's skin with the plastic sheet.

When a surgical drape is placed over a patient, much of the drape will slope relatively steeply away from the horizontal. Blood or liquid that flows from the surgical area and lands on these vertically sloping parts of the drape will endeavour to run down along the drape gravitationally, wherewith the spread pattern of fluid absorbed on such parts will have a substantially vertical extension. This constitutes a problem, since it is desirable for fluid flowing from the surgical wound or area to be absorbed in those parts of the drape that lie nearest the surgical area and therewith reduce the risk of personnel or instruments coming unintentionally into contact with blood that has been absorbed by the liquid-absorbent top sheet. One way of solving this problem is to provide liquid barriers in the form of upstanding pleats or folds in the drape material; see U.S. Pat. No. 4,873,997. According to WO-A1-95/10242, the problem is solved by placing threads or similar elements between the top sheet and the liquid-impervious sheet One drawback with these solutions is that they make manufacture of the surgical drape more difficult and more expensive. There is thus a need for a liquid barrier element that can be included in a surgical drape in a manner which will not make the drape manufacturing process more difficult to carry out or disturb said process.

An object of the present invention is to satisfy this need.

SUMMARY OF THE INVENTION

This object is achieved in accordance with the invention with a surgical drape of the kind described in the introduction that is characterised by at least one string or bead of hotmelt glue disposed on one surface of the surgical drape, and in that the hotmelt glue extends from the upper side of the top sheet and through said top sheet and is fastened to the liquid-impervious sheet Such strings can be produced very simply, by placing the string in a molten phase on the surface of the drape and thereafter pressing the string through the top sheet into abutment with the liquid-impervious sheet with the aid of a roller or like pressure means.

In one preferred embodiment of the invention, each string of hotmelt glue extends in a direction generally parallel with one edge of the drape and has a generally rectilinear extension. In one variant, at least one string of hotmelt glue is disposed on each side of two mutually opposing edges of an opening formed in the drape, between respective edges of the opening and corresponding edges of the drape.

In another variant, the string or strings of hotmelt glue is/are curved.

BRIEF DESCRIPTION OF THE DRAWINGS

The present invention will now be described in more detail with reference to an exemplifying embodiment thereof and also with reference to the accompanying drawings, in which.

DESCRIPTION OF EMBODIMENTS

Figure 1:
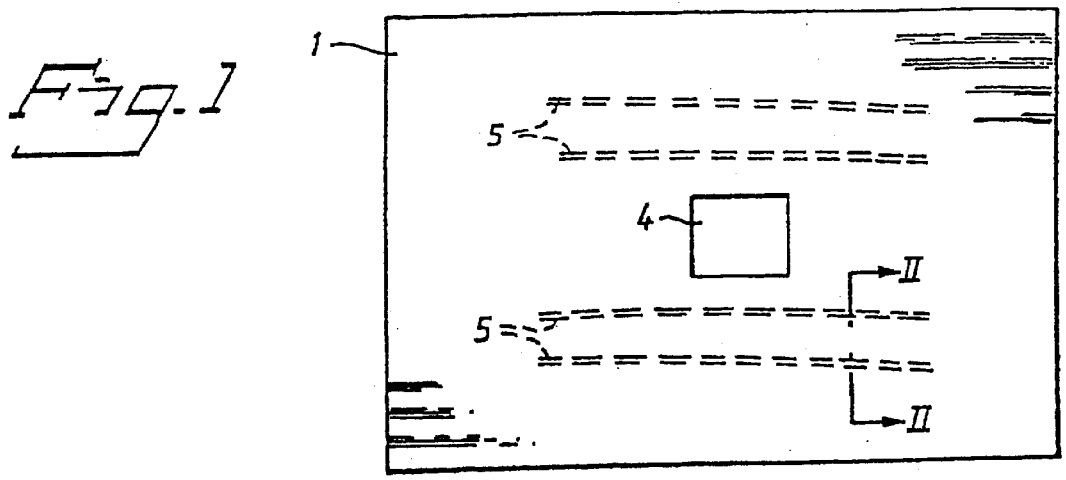
FIG. 1 illustrates an embodiment of an inventive surgical drape schematically and from above.

The surgical drape in the Figures is built-up in the same way as the drape retailed by Applicant under the trademark Klinidrape®, and includes an liquid-absorbent top sheet 1, a liquid-impervious intermediate sheet 2, and an absorbent bottom sheet 3. The sheet includes an opening 4 which is intended to be placed over the surgical area In the case of the illustrated preferred embodiment of an inventive surgical drape, strings 5 of hotmelt glue are disposed on the drape generally parallel with two mutually opposing edges of the drape. In this case, the strings 5 extend in the longitudinal direction of the drape, on respective sides of the opening 4.

The strings 5 are applied in a molten state in a desired pattern on the upper side of said drape during its manufacture. The strings 5 are then pressed down into and through the top sheet 1 and into abutment with the intermediate sheet 2, with the aid of a roller or some like pressure means. Because the strings are pressed into abutment with the sheet 2, it is ensured that no gaps or the like will be found between the strings 5 and the sheet 2. This effectively prevents liquid on the surface of the sheet 2 from passing beyond the strings 5. The strings 5 function as flow barriers and force at least some of the liquid that flows in a direction towards the element/?/ to change direction and flow in a direction that is essentially parallel with the longitudinal direction of the glue sting.

Figure 2:
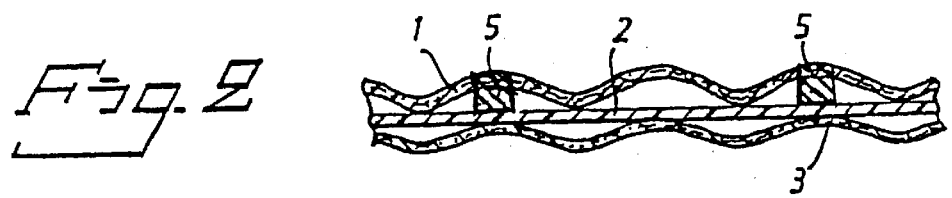
FIG. 2 is a cross-sectional view taken on the line II—II in FIG. 1.
Figure 3:
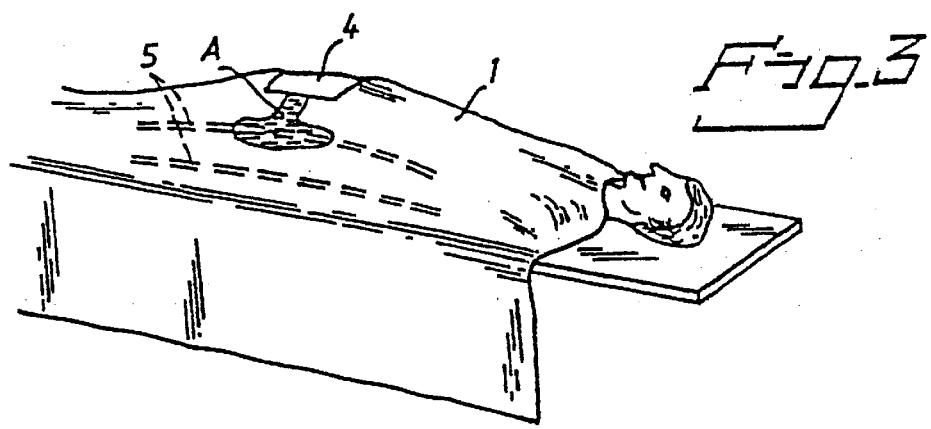
FIG. 3 shows the drape in FIG. 1 placed on a patient.

FIG. 3 shows the drape of FIGS. 1 and 2 placed over a patient, with the opening 4 positioned in the region where surgery is to take place, which in the illustrated case is in the abdominal region of the patient Those parts of the surgical drape that lie outwardly of the patient's sides will slope comparativly steeply in relation to the horizontal, meaning that gravity will greatly influence the way in which liquid spreads on these parts of the drape. Liquid present on a horizontal absorbent surface of a surgical drape of the Klinidrape® kind will spread radially from the wetting point so as to form a generally circular spread pattern, while liquid present on a surface that slopes relative to the horizontal will spread downwards to a extent that increases in keeping with an increasing angle of slope, so as to form a droplet-like spread pattern with the narrow end of the droplet pointing downwards. In the case of the described surgical drape, however, the strings 5 will produce the spread pattern referenced A when liquid or fluid flowing from the surgical area reaches one of the strings 5, which stops downward movement of the liquid and causes the liquid to flow in the longitudinal direction of the string, as shown in FIG. 3. When large quantities of liquid, e.g. blood or irrigation fluid, flow from the surgical area, some of the liquid/fluid will pass the upper string of the strings 5 shown in FIG. 3 and will then be stopped by the lower string. This results in a more favourable spread pattern and enables a larger part of the absorbent surface of the drape to be engaged in absorbing the liquid emitted.

In the case of the embodiment illustrated in the Figures, the strings 5 are disposed solely on those parts of the drape that lie along the sides of the patient when the drape is placed in position, since remaining parts of the drape either do not slope to an extent at which the spread pattern will be affected unduly by gravity, or are followed by generally horizontal drape parts that provide a favourable spread pattern. In the case of those parts of the drape which lie on one side of the opening edges that extend parallel with the transverse edges of the drape, the effect of gravity may, on the other hand, be to advantage since this will promote spreading of the liquid in the longitudinal direction of the drape in these parts thereof Although the strings 5 are only shown to extend over a part of the length of the drape, it will be understood that these strings may extend along the full length of the drape if so desired It should be mentioned in this respect that positioning of the strings will, of course, depend on the kind of surgical operation to be performed, and that in the case of other surgical drape configurations intended for other kinds of surgery it may be appropriate to place the strings transversely across the drape or even around the perimeter of the drape in a manner to obtain suitable spread patterns. The number of strings used may also vary within the scope of the invention. For instance, the strings may be arranged in a chequered pattern over the whole of the drape, although only those strings that extend transversely of the drape flow direction when the drape is in use will have the aforesaid effect.

Figure 4:
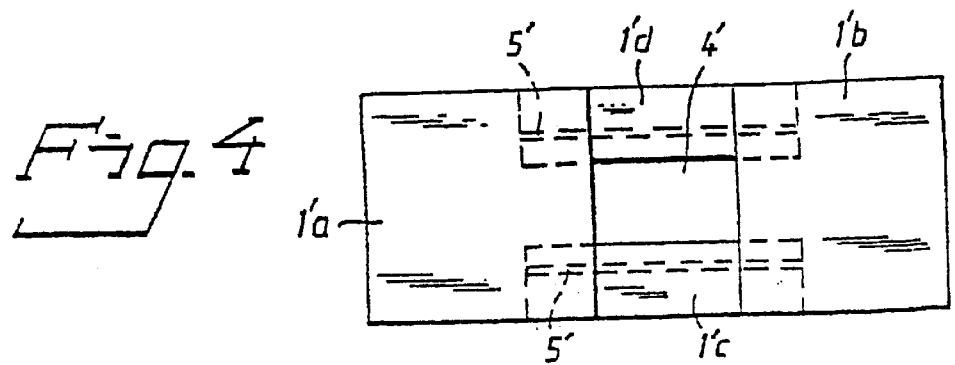
FIG. 4 illustrates an embodiment of an inventive surgical drape that is comprised of four parts.

FIG. 4 shows a surgical drape that is comprised of four separate parts, exemplified in the Figure by the top sheet parts 1'*a*, 1'*b*, 1'*c* and 1'*d* which have been arranged to form an opening 4' in the surgical area As will be seen from the Figure, strings 5' are disposed in the side parts 1'*c*, 1'*d*.

It will be understood that the described embodiment can be modified in several ways without departing from the scope of the invention. For instance, the strings may be curved instead of essentially rectilinear as in the drawing, and neither need the strings extend parallel with the longitudinal or transversal edges of the drape. The main criterion is that those parts of the drape which slope in relation to the horizontal when the drape is used extend at an angle to the gravitational force projection in the plane in which the string-carrying parts of the drape lie. It may be sufficient in many cases to apply a longitudinal string on each side of the longitudinal symmetry line of the drape. The invention can also be applied to surgical drapes that lack a bottom absorbent comfort layer. It will therefore be understood that the invention is restricted solely by the contents of the following Claims.

What is claimed is:

1. A surgical drape that includes a liquid-absorbent top sheet (1) and a liquid-impervious sheet (2) immediately beneath said top sheet, said liquid-impervious sheet facing towards a patient when the drape is in use, characterised in that at least one string of hotmelt glue (5) is disposed on the surface of the drape; and in that the hotmelt glue extends from the upper side of the top sheet, through said top sheet and bonds with the liquid-impervious sheet.

2. A surgical drape according to claim 1, characterised in that each string of hotmelt glue (5) extends in a direction that is generally parallel to one edge of the drape.

3. A surgical drape according to claim 1, characterised in that the hotmelt glue string or strings (5) has/have a generally rectilinear extension.

4. A surgical drape according to claim 1, characterised in that the hotmelt glue string or strings (5) has/have a curved extension.

5. A surgical drape according to claim 1, characterised in that at least one hotmelt glue string (5) is disposed on each side of two mutually opposing edges of an opening (4) provided in the drape, between respective edges of the opening and corresponding edges of the drape.

\* \* \* \* \*